(12) United States Patent
Yuan

(10) Patent No.: US 6,485,575 B2
(45) Date of Patent: *Nov. 26, 2002

(54) STARCH-EMULSIFIER COMPOSITION AND METHOD OF MAKING

(75) Inventor: Chienkuo Ronnie Yuan, Chelmsford, MA (US)

(73) Assignee: Opta Food Ingredients, Inc., Bedford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/001,943

(22) Filed: Oct. 23, 2001

(65) Prior Publication Data

US 2002/0152931 A1 Oct. 24, 2002

Related U.S. Application Data

(63) Continuation of application No. 09/488,128, filed on Jan. 20, 2000, now Pat. No. 6,306,218, which is a continuation of application No. 09/082,345, filed on May 20, 1998, now Pat. No. 6,017,388, which is a continuation-in-part of application No. 08/783,574, filed on Jan. 15, 1997, now Pat. No. 5,755,890.
(60) Provisional application No. 60/010,061, filed on Jan. 16, 1996.

(51) Int. Cl.$^7$ .......................... C08B 30/14; A23L 1/035; C08J 3/215; C08L 3/02

(52) U.S. Cl. ................. 127/71; 106/162.81; 106/205.7; 106/205.71; 106/206.1; 106/215.4

(58) Field of Search ...................... 127/21; 106/162.81, 106/205.7, 205.71, 206.1, 215.4

(56) References Cited

U.S. PATENT DOCUMENTS

| | | | |
|---|---|---|---|
| 4,260,642 A | 4/1981 | Mitchell et al. | ............ 426/579 |
| 4,491,483 A | 1/1985 | Dudacek et al. | .............. 127/33 |
| 4,499,116 A | 2/1985 | Zwiercan et al. | ........... 426/582 |
| 4,971,723 A | 11/1990 | Chiu | ........................ 252/315.3 |
| 5,100,475 A | 3/1992 | Würsh et al. | ................. 127/67 |
| 5,185,176 A | 2/1993 | Chiu | .......................... 426/651 |
| 5,281,432 A | 1/1994 | Zallie et al. | ................. 426/549 |
| 5,291,877 A | 3/1994 | Conde-Petit et al. | .......... 127/33 |
| 5,409,726 A | 4/1995 | Stanley et al. | ............... 426/573 |
| 5,755,890 A | * 5/1998 | Yuan | ........................... 127/71 |
| 6,017,388 A | 1/2000 | Yuan | ........................ 106/210.1 |
| 6,228,419 B1 | 3/2001 | Yuan | .......................... 426/661 |

FOREIGN PATENT DOCUMENTS

| | | | |
|---|---|---|---|
| EP | 0011479 A1 | 5/1980 | |
| EP | 0076381 A2 | 8/1982 | ............ A23L/1/195 |
| EP | 0150715 A2 | 1/1985 | ............ C08B/30/14 |
| EP | 0519104 B1 | 6/1991 | .......... A23L/1/0522 |
| FR | 2629684 | 10/1989 | |
| WO | WO 94/09645 | 5/1994 | |

OTHER PUBLICATIONS

G.I. Galloway, et al., "Properties and Structure of Amylose–Glyceryl Monostearate Complexes Formed in Solution or On Extrusion of Wheat Flour," *Journal Food Science* 54(4):950–957 (1989) No Month Provided.

M.G. Godet et al., "Crystalization of Amylose–Fatty Acid Complexes Prepared With Different Amylon Chain Lengths," *Carbohydrate Polymers* 27:47–52, (1995) No Month Provided.

Seneviratne and Biliaderis, "Action of α–Amylase or Amylose–Lipid Complex Superstructures," *Journal of Cereal Science* 13:129–143 (1991) No Month Provided.

Biliaderis, C.G. et al., "On the Multiple Melting Transitions of Starch/Monoglycerides Systems," *Food Chem.* 22:279–295, (1986) No Month Provided.

Biliaderis, C.G., et al., "Non Equilibrium Melting of Amylose–V Complexes," *Carbohydr. Polym.* 6:269–288 (1986) No Month Provided.

Biliaderis, C.G. et al., "Thermal Behavior of Amylose–Lipid Complexes," *Carbohydr. Polym.* 5:367–389, (1985) No Month Provided.

Biliaderis and Seneviratne, "On the Supermolecular Structure and Metastability of Metastability of Glycerol Monostearate–Amylose Complex," *Carbohydr. Polym.* 13:185–206 (1990) No Month Provided.

Eliasson and Krog, "Physical Properties of Amylose–Monoglyceride Complexes," *J. Cereal Sci.* 3:239–248 (1985) No Month Provided.

Karkalas and Raphaelides, "Quantitative Aspects of Amylose–Lipid Interactions," *Carbohydr. Res.* 157:215–234 (1986) No Month Provided.

Kowblansky, M., "Calorimetric Investigation of Inclusion Complexes of Amylose with Long–Chain Aliphatic Compounds Containing Different Functional Groups," *Macromolecules* 18:1776–1779 (1985) No Month Provided.

Deffenbaugh et al., "Use of the Rapid Visco–Analyzer to Measure Starch Pasting Properties", *Stärke (Starch )* 42(3):89–95 (1990) No Month Provided.

Stoichi et al., "Method for Dissolving Starch" *Patent Abstracts of Japan*, 095(003):JP 06 345802 (Apr. 28, 1995).

Goto et al., "Starch Additives to Food for Frying", *Chemical Abstracts*, 124(15): 200687 (Apr. 9, 1996).

Neumüller O–A, et al., "Völlig neubearbeitete und erweiterte siebte Auflage des von," *Stärke* 3305–3307 (1975).

Robyt, J.F., "Enzymes in the Hydrolysis and Synthesis of Starch" In *Starch: Chemistry and Technology.* R.L. Whistler, et al., eds. (NY: Academic Press, Inc.), pp. 87–89, 94 (1984).

* cited by examiner

*Primary Examiner*—David Brunsman
(74) *Attorney, Agent, or Firm*—Hamilton, Brook, Smith & Reynolds, P.C.

(57) ABSTRACT

A method of producing starch-emulsifier compositions by heating a starch in the presence of an emulsifier to form a complex with unique properties. The product can be further treated to obtain greater than about 20% short chain amylose. Starch-emulsifier compositions (e.g., powders, gels, pastes) produced by this method and food products containing the starch-emulsifier composition are also described.

25 Claims, No Drawings

STARCH-EMULSIFIER COMPOSITION AND METHOD OF MAKING

RELATED APPLICATIONS

This is a Continuation application of U.S. application Ser. No. 09/488,128, filed Jan. 20, 2000 (U.S. Pat. No. 6,306,218, issued Oct. 23, 2001), which is a Continuation application of U.S. application Ser. No. 09/082,345, filed May 20, 1998 (U.S. Pat. No. 6,017,388, issued Jan. 25, 2000), which is a Continuation-in-Part of U.S. application Ser. No. 08/783,574, filed Jan. 15, 1997 (U.S. Pat. No. 5,755,890, issued May 26, 1998), which claims priority to Provisional Application No. 60/010,061, filed on Jan. 16, 1996. The entire teachings of which are incorporated herein by reference.

BACKGROUND OF THE INVENTION

Starch is composed primarily of two components: amylose, a mainly linear polymer of about 500–6000 $\alpha$-D glucosyl residues, and amylopectin, a highly branched polymer of $\alpha$-D glucosyl distributed in 15–60 residues per chain (Godet et al., *Carbohydrate Polymers* 27:47–52 (1995)). It is well known that amylose can form complexes with molecules such as iodine, alcohols and lipids, whereas amylopectin forms these complexes weakly or not at all (Morrison et al., *Cereal Chem* 70:385–91 (1993); Sarko & Zugenmaier, *Fiber Diffraction Methods*, A. D. French & K. C. Gardner, Eds., ACS Symposium Series 141:459–482 (1980)). The in situ biosynthesis of amylose-lipid complexes in starch with naturally occurring fatty acids and phospholipids has been demonstrated (Morrison et al. (1993)). Others have shown that complex formation occurs during heat/moisture treatments, especially during gelatinization of starches with the naturally containing lipids (Kugimiya et al., *Stärke* 32:265–270 (1980); Kugimiya & Donovan, *J. Food Sci.* 46:765–777 (1981)) or when lipids are added to defatted starches (Biliaderis et al., *Food Chem.* 22:279–295 (1986)) or pure amylose which is free of natural lipids (Biliaderis et al, *Carbohydr. Polym.* 5:367–389 (1985)).

Both naturally-occurring and heat-formed complexes show specific properties such as a decrease in amylose solubility or an increase in gelatinization temperatures (Eliasson et al., *Stärke* 33:130 (1981), Morrison et al. (1993)). Polar lipids, e.g., fatty acids and their monoglyceride esters are of technological importance in starch systems, as they cause a reduction in stickiness, improved freeze-thaw stability (Mercier et al., *Cereal Chem.* 57:4–9 (1980) and retardation of retrogradation. One important example is the use of fatty acids and monoglycerides as anti-staling agents in bread and biscuits. Incorporation of such additives in the dough induces a slower crystallization (retrogradation) of the amylose fraction and retards the staling of bread (Krog, *Stärke* 22:206–210 (1971)).

SUMMARY OF THE INVENTION

The present invention pertains to starch-emulsifier compositions and methods of making the starch-emulsifier compositions comprising heating starch (e.g., jet-cooking, heating in a batch cooker) in the presence of an emulsifier to produce a starch-emulsifier dispersion which can optionally be treated to obtain greater than about 20% by weight short chain amylose.

In one embodiment of the invention, a starch and an emulsifier are heated (e.g., jet-cooked) to disrupt essentially all starch granules and solubilize amylose and amylopectin in the starch. The product contains a dispersion of gelatinized starch and emulsifier which is believed to be in the form of a complex, as seen by X-ray diffraction. The dispersion of starch and emulsifier can be cooled slowly or quickly to form an elastic textured paste, or the solution can optionally be dried to a powder.

In another embodiment of the invention, a starch and emulsifier are heated (e.g., jet-cooked) to produce a dispersion of gelatinized starch and emulsifier in which the amylose and amylopectin are solubilized. The starch is subsequently hydrolyzed to release short chain amylose, preferably using an enzymatic treatment. After hydrolysis of the starch-emulsifier solution, the solution can optionally be heated to a temperature sufficient to liquify the emulsifier, thereby increasing the percentage of starch-emulsifer complex formed. Thereafter, the solution can be cooled to form a short-textured, non-elastic paste or it can optionally be dried (e.g., by spray drying) into a powder.

The starch-emulsifier compositions can also be optionally co-processed with hydrocolloids, polymers, gums, modified starches and combinations thereof, which can be added at any point in the processes described herein. These optional ingredients serve to change (e.g., increase or decrease) the functional properties (e.g., water binding capacity, oil binding capacity or viscosity) of the composition depending upon product end use. For example, these optional ingredients can be added to increase the overall water binding capacity of the starch-emulsifier composition or change the rheology of the starch-emulsifier composition.

The starch-emulsifier composition produced by a process which uses a hydrolytic method is characterized by a relatively small particle size (a weight average of 4–5 $\mu$), a short, non-elastic texture or rheology and a low water and oil binding capacity. The starch-emulsifier composition produced by cooking starch and emulsifier, without subsequent hydrolysis, is characterized as more elastic and a less opaque gel compared to the hydrolyzed product. In either process, the dried starch-emulsifier composition can be rehydrated, preferably in an aqueous medium suitable for use in food or beverage formulations (e.g., milk or water), under conditions of medium to high shear to produce an opaque paste upon refrigeration.

The starch-emulsifier compositions produced by the methods described herein are useful in a variety of food and beverage applications. For example, the starch-emulsifier compositions can be used as an opacifier in foods and beverages such as skim milk, or as a texturizing agent to prepare dairy products with a rheology similar to sour cream, yogurt, mayonnaise and similar products. For example, the starch-emulsifier compositions of the present invention can be used to prepare lactose-free dairy products. The starch-emulsifier compositions can also be used to stabilize foams, such as in the production of ice cream, and as a fat replacer in a variety of reduced-fat and fat-free foods, such as cakes, pudding type desserts, sauces, margarine, cream cheese and other spreads, snack dips, mayonnaise, sour cream, yogurt, ice cream, frozen desserts, fudge and other confections, and skim milk. The starch-emulsifier compositions can be incorporated into fat-free, reduced fat and fat containing cheeses, such as natural, processed and imitation cheeses in a variety of forms (e.g., shredded, block, slices, grated). The starch-emulsifier compositions are also useful, as for example a shortening, in baked goods such as cakes, pies, brownies, cookies, breads, noodles, snack items, such as crackers, graham crackers and pretzels, and similar products.

DETAILED DESCRIPTION OF THE INVENTION

The present invention pertains to methods of manufacture and the starch-emulsifier compositions produced thereby that are useful in a variety of food and beverage applications. According to the invention, a starch is heated in the presence of an emulsifier to a temperature and pressure sufficient to disrupt essentially all the starch granules and solubilize the amylose and amylopectin contained therein, such as by jet cooking, to yield a starch-emulsifier dispersion. This dispersion can be cooled slowly or quickly to form an elastic gel, or the dispersion can optionally be dried to a powder. The powder can be rehydrated with medium to high shear to produce a smooth gel that is more elastic and less opaque compared to the hydrolyzed product described below.

Alternatively, a dispersion of the starch-emulsifier complex produced as described above can be treated to generate about 20% by weight short chain amylose (e.g., enzymatically debranched, hydrolysis of the backbone by amylase or acid hydrolysis), and the resultant dispersion of starch, containing greater than about 20% by weight short chain amylose, and emulsifier is optionally heated to a temperature sufficient to inactivate the enzyme if used and to liquify the emulsifier. Liquification of the emulsifier facilitates the formation of additional starch-emulsifier complexes in the final composition.

As used herein, short chain amylose is defined as amylose having a degree of polymerization (DP) of from about 6 to about 60 and a molecular weight of from about 1,000 to about 10,000 which is indicative of maltodextrin. The term "gelatinization" or varient thereof, is intended to embrace the generally recognized term but also is intended to encompass the process of rupturing essentially all starch granules present in the starch, thereby releasing amylose and amylopectin.

The dispersion of starch and emulsifier containing about 20% short chain amylose can be allowed to cool to form an opaque paste with a short, non-elastic texture. Alternatively, the dispersion can be dried to a powder and rehydrated with medium to high shear to produce a short, smooth, non-elastic textured paste of high opacity upon refrigeration.

The starch used as a starting material in the process of the present invention can be a native starch or a pregelatinized starch. If a pregelatinized starch is utilized, it should preferably contain a low amount of resistant starch, such as less than about 10% resistant starch. If the starting starch has more than about 10% resistant starch, the starch can be used in the present invention if it is first heated to a temperature above the melting point of the resistant starch.

The native or pregelatinized starch used in the present invention should preferably have an amylose content of less than about 30%. If the amylose content is greater than about 30%, debranching and/or hydrolysis of the starch (e.g., with an acid or by enzymatic amylase treatment) prior to heating in the presence of the emulsifier may be required to reduce the molecular weight of the amylose. The use of high-amylose starch is generally not preferred, as high-amylose starch tends to form stable resistant starch with a large particle size during processing. For example, debranched or partially hydrolyzed amylomaize can be used, as well as common cornstarch, potato, tapioca, wheat, smooth pea, rice, sago, barley and oat starches.

Without wishing to be bound by theory, it is believed that the processes described herein yield compositions comprising starch and emulsifier in the form of a complex having an insoluble microparticle nature which is stabilized by the interaction between amylose and emulsifier. The composition also comprises uncomplexed emulsifier, uncomplexed starch, and optionally short chain amylose if debranching and/or hydrolysis is performed. Thus, emulsifiers capable of forming a complex with amylose are particularly preferred for use in the invention. Generally, the emulsifiers will be monoglycerides, sorbitan esters, diacetyl tartaric acid esters of monoglycerides (DATEM), propylene glycol esters, enzyme modified lecithin (EML), polysorbates and sucrose esters of medium and long chain saturated fatty acids (e.g., having an acyl group containing more than about 10 carbon atoms), as well as saturated fatty acids (e.g., saturated fatty acids which contain from about 12 to about 18 carbons) and unsaturated fatty acids (unsaturated fatty acids which contain from about 12 to about 18 carbons, e.g., oleic and linoleic acids). For example, emulsifiers including, but not limited to, polyethylene glycol monolaurate or glyceryl monostearate, sodium or calcium stearoyl-2-lactylate, polyoxyethylene sorbitan monostearate, sucrose monostearate and sucrose monopalmitate are suitable for use in the starch-emulsifier composition of the present invention, as well as other saturated fatty acids (see also Example 6). EML can be produced by treating lecithin with phospholipase A2. EML produced through the action of phospholipase A2 is enriched in lysophosphatydylcholine, which is known to form complex with amylose. Commercial EML is available at Lucas Meyer Inc. (Decatur, Ill.) and Central Soya Co. (Fort Wayne, Ind.).

The starch and the emulsifier are combined in an aqueous medium such as water to produce a dispersion. The dispersion generally contains from about 5% to about 25% (w/w) of starch. The emulsifier will be present in an amount which is approximately 0.1% to about 25% of the starch weight, and more preferably 1% to 10% of the starch weight present in the composition. The dispersion is then heated under conditions appropriate to disrupt essentially all the starch granules and solubilize the amylose and amylopectin present in the starch. This can be carried out, for example, by co-jet cooking the starch-emulsifier dispersion. Alternatively, the starch-emulsifier dispersion can be heated in a reactor or batch cooker, or by any other method in which the starch is gelatinized in the presence of the emulsifier, such as by extrusion. The starch can also be jet cooked into the emulsifier; that is, the starch can be heated to or above its gelatinization temperature and immediately combined with the emulsifier. The emulsifier may need to be dispersed beforehand in a little water and the dispersion added to the starch slurry prior to cooking; added to the jet cooked starch; or the starch is jet cooked into the dispersion of the emulsifier. The temperature and pH necessary to disperse the emulsifier in water are characteristic for each emulsifier or can be determined by those skilled in the art. It is essential that the emulsifier and starch be combined prior to the heating or jet cooking step or immediately after solubilization of the starch, as later addition of the emulsifier results in a larger particle size and a gritty product due to retrogradation of the starch.

In one embodiment, after the starch-emulsifier dispersion is heated to solubilize the amylose present in the starch, the starch is treated to release short chain amylose. Appropriate treatment of the starch will result in a starch material containing greater than about 20% short chain amylose. Generally, release of the short chain amylose from the starch will be carried out by enzymatically debranching the starch, e.g., the starch can be debranched with (1–6)-specific glycosidic enzymes which are capable of cleaving 1,6-alpha-D-glucosidic linkages. For instance, the starch-emulsifier dispersion can be treated with pullulanase or isoamylase, at a temperature and pH and for a time sufficient to allow the enzyme to release the short chain amylose. Generally, appropriate temperatures will range from about 25° C. to about 100° C., with from about 55° C. to about 65° C. being preferred, for a time of from about 1 hour to about 30 hours, depending on the enzyme utilized and the enzyme concentration. Furthermore, the pH of the solution will be from about 3 to about 7.5. In a particularly preferred method, the starch-emulsifier dispersion is treated with pullulanase at 60° C. at pH 5 for about 4 hours. The optimum conditions for the enzymatic reaction will vary, with changes in parameters such as starch and enzyme concentrations, pH, temperature and other factors which can be readily determined by the skilled artisan.

Alternatively, the starch can be randomly hydrolyzed to produce greater than 20% short chain amylose by use of an appropriate acid, such as a mineral acid or organic acid. Generally, acid hydrolysis will take place at a pH of less than about 4° C. and at a temperature greater than about 60° C., depending upon the acid used. The conditions for acid hydrolysis should be such that inappropriate side reactions are minimized. Short chain amylose can also be generated by treating the starch with alpha amylase, alone or in combination with pullulanase. Substantial debranching or hydrolysis of the starch (e.g., debranching sufficient to generate a starch material containing greater than about 20% short chain amylose) results in a short textured, non-elastic paste, whereas in the absence of debranching or hydrolysis the product is an elastic gel (see Example 3).

Both the hydrolyzed and non-hydrolyzed starch-emulsifier dispersions can be heated to a temperature and pH and for a time sufficient to liquify the emulsifier, i.e., a temperature above the melting point of the emulsifier, to produce additional starch-emulsifier complexes in the composition. If a debranching enzyme is used, the heat treatment will also inactivate the enzyme. In most cases, a temperature of approximately 70° C. to approximately 100° C. is sufficient to liquify the emulsifier within the dispersion and inactivate the enzyme, if present. The starch-emulsifier dispersion can be heated by a number of conventional methods, including a heat exchanger, jacketed reactor, direct steam injection or extruder.

The starch-emulsifier compositions that have been hydrolyzed and subsequently heat treated appear watery and have a low viscosity at approximately 10% to 25% solids. The low viscosity product can be cooled slowly or rapidly to form a paste for use in food applications, or the low viscosity composition can be optionally dried to produce a powder by a number of art-recognized methods, including spray drying, belt drying, freeze drying, drum drying or flash drying; however, in a preferred embodiment, the dispersion is spray dried. The powder can be stored at room temperature, and can be rehydrated with water or another aqueous medium, preferably an aqueous medium which is appropriate for use in food and beverage formulations, under conditions of medium to high shear to give a paste of high opacity and short, non-elastic texture.

The starch and emulsifier can also be co-processed with hydrocolloids, gums, polymers, modified starches and combinations thereof to change the rheology or increase the water binding capacity of the starch-emulsifier compositions. For example, xanthan gum, alginate, carrageenan, carboxymethyl cellulose, methyl cellulose, guar gum, gum arabic, locust bean gum and combinations thereof can be added to the starch-emulsifier compositions at any time during the preparation thereof, as long as the additional ingredient(s) does not prevent the formation of the amylose-emulsifier complex. That is, these additional optional ingredients can be jet-cooked along with the starch and emulsifier, added prior to or after the debranching step, added prior to or after the optional heating step, added to the paste composition or dry blended with the powdered composition after drying. Preferably, the hydrocolloid, gum, modified starch or polymer is added to the dispersion after the debranching step and prior to drying the composition (see Example 7) or is dry blended with the powdered composition after the drying step.

The starch-emulsifier compositions of this invention comprise starch-emulsifier complexes, uncomplexed emulsifier, uncomplexed starch and optionally greater than from about 20% short chain amylose if the uncomplexed starch in the composition is hydrolyzed. The percentage of complex present in the composition will vary depending upon whether the starch and emulsifier are hydrolyzed, but in any event, the composition should comprise a minimum of about 20% by weight starch-emulsifier complex. The complexes are insoluble microparticulates which have an average particle size of less than about 10 $\mu$, and preferably less than about 6 $\mu$. The starch-emulsifier composition of the present invention produced using hydrolysis has a short, non-elastic texture or rheology and a low water and oil binding capacity and contains greater than about 20% short chain amylose. The starch-emulsifier composition produced by cooking starch and emulsifier, without subsequent hydrolysis, is characterized as a more elastic and less opaque gel compared to the hydrolyzed product.

The starch-emulsifier compositions of the present invention are suitable for use in a variety of foods and beverages. The amount of starch-emulsifier composition incorporated into the food or beverage will depend upon the formulation of the food, but will generally be approximately 1–10% by weight. For example, the starch-emulsifier compositions can be used as an opacifier in milk and similar foods to improve the visual appeal of the food. The starch-emulsifier compositions can also be used as a texturizing agent in various dairy foods; due to its small particle size, the starch-emulsifier compositions do not impart a gritty mouthfeel to products in which it is incorporated. The starch-emulsifier compositions are useful for preparing dairy products with a rheology similar to traditional sour cream, yogurt and mayonnaise formulations. For example, the starch-emulsifier compositions can be used in the preparation of lactose-free dairy products. The compositions are particularly useful for the preparation of reduced-fat and fat-free food products, particularly margarines, pudding type desserts, sauces, snack dips, mayonnaise, sour cream, yogurt, ice cream, frozen desserts, cream cheese and other spreads, fudge and other confections, and skim milk. The starch-emulsifier compositions can be incorporated into fat-free, reduced fat and fat containing cheeses, such as natural, processed and imitation cheeses in a variety of forms (e.g., shredded, block, slices, grated). The starch-emulsifier compositions are also useful in baked goods such as breads, cakes, pies, brownies, cookies, noodles, snack items, such as crackers, graham crackers and pretzels, and similar products, as it does not interfere with the organoleptic properties of the foods in which it is incorporated.

Terms used herein have their art-recognized meaning unless otherwise defined. The teachings of references referred to herein are incorporated herein by reference. All percentages are by weight unless otherwise specified.

The following examples are offered for the purpose of illustrating the present invention and are not to be construed to limit the scope of the present invention:

EXAMPLES

Example 1
Effect of Different Levels of Monoglyceride on Starch-Emulsifier Composition Fifteen gallons (55 liters) of corn starch slurry (15% solids) and various levels of distilled monoglyceride emulsifier (Myverol 18-06, Quest International; containing 90% glyceryl monostearate) were preheated to 60° C. in a Likwifier. The slurries were then pumped through a jet cooker operating at 150° C. and 120 psi steam pressure. Each jet cooked dispersion was then cooled to 60° C. and the pH was adjusted to 5.2±0.2 using 15% phosphoric acid. The starch-emulsifier dispersion was enzymatically debranched by the enzyme pullulanase (Promozyme 200 L, Novo Nordisk A/S, Denmark; 0.02 ml enzyme per gram of starch solids) at 60° C. for 4 hours. The debranched starch product was then heated to 90° C. and spray dried into a fine powder. The spray drier air inlet and outlet temperatures were typically 360° F. (182° C.) and 220° F. (104° C.), respectively. Four samples were prepared as described above with different monoglyceride contents:

Sample A: no monoglyceride added
Sample B: 1% (of starch weight) monoglyceride added
Sample C: 3% (of starch weight) monoglyceride added
Sample D: 6% (of starch weight) monoglyceride added.

Example 2
Characterization of the Starch-Emulsifier Composition

The four samples prepared according to example 1 were analyzed by differential scanning calorimeter (DSC), molecular weight distribution, X-ray diffraction analysis, particle size distribution, gel viscosity, and opacity.

A. DSC Thermal Analysis

Ten milligrams of powdered sample was weighed in a Perkin Elmer high pressure capsule DSC pan. The sample was mixed with 50 μl deionized water and hermetically sealed in the DSC pan. The sample was then analyzed (DSC 7, Perkin-Elmer, Norwalk, Conn.) from 20° C. to 160° C. at 10° C./minute with a sealed empty pan as a reference. Samples B, C and D showed an endothermic peak at about 105° C., typical of the melting of amylose-lipid complexes.

After the initial scan the samples were quench cooled from 160° C. to 20° C. in the DSC, followed by rescanning from 20° C. to 160° C. at 10° C/min. Samples B, C and D all showed a peak near 100° C. to 102° C. upon rescanning, confirming the presence of amylose-lipid complex.

B. Molecular Weight Distribution

The molecular weight distributions of the debranched samples were analyzed by high performance size-exclusion chromatography (HPSEC). Two Polymer Laboratory mixed bed B columns (300×7.5 mm) were connected in series and the temperature of the column maintained at 70° C. The mobile phase was 5 mM sodium nitrate in DMSO at a flow rate of 1 ml/minute. A Waters 400 refractive index detector was used. The columns were calibrated using pullulan standards (Hayashibara Biochemicals, Japan) with molecular weights ranging from 5800 to $1.66 \times 10^4$ daltons. The molecular weights of the starch samples were obtained using Perkin Elmer's Turbochrome 4 software and the calibration curve for the standards. The starch samples (10 mg) were completely dissolved in 4 ml mobile phase by heating in a 90° C. water bath for 10 minutes. A 200 μl sample was injected onto the columns. In general the chromatograms of the 4 samples prepared according to Example 1 can be divided into two fractions: high molecular weight (HMW) and low molecular weight (LMW). The molecular weight distribution data are summarized in Table 1. The results indicate that the molecular weight distributions were essentially the same for the four samples.

TABLE 1

| Sample | HMW Mw | HMW Mn | LMW Mw | LMW Mn | % area of LMW |
|---|---|---|---|---|---|
| A | 470 kd | 114 kd | 3.7 kd | 2.5 kd | 35 |
| B | 582 kd | 119 kd | 3.7 kd | 2.5 kd | 35 |
| C | 569 kd | 119 kd | 3.6 kd | 2.5 kd | 37 |
| D | 579 kd | 109 kd | 3.6 kd | 2.5 kd | 34 |

C. X-ray Diffraction Analysis

X-ray diffraction diagrams of samples A, C (as described in Example 1) and a dry blend of sample A with 3% monoglyceride (based on starch weight, Myverol 18-06, Quest International) were recorded using a X-ray diffractometer (Philips Electronic Instruments) with $CuK_{\alpha 1}$ radiation (0.15405 nm). The generator was operated at 40 KV and 30 mA. The scans were recorded from 2 to 30° 2-theta at a rate of 1° per minute. Scans for sample A and the dry blend with monoglyceride were virtually identical, showing mostly amorphous patterns. The scan for sample C showed 3 distinctive peaks near 7.36, 13.1, and 20.1° 2-theta, characteristic of the crystalline patterns for amylose-lipid complex as reported by Biliaderis and Seneviratne (*Carbohydrate Polymer*, 13:185–206 1990).

D. Particle Size Distribution

The particle size distribution was determined by using a laser light particle size analyzer (Microtrac, Leeds and Northrup Instruments, North Wales, Pa.). A 15% (w/w) dispersion of each starch sample was prepared by mixing the sample in 70° C. deionized water using a kitchen blender at high speed for 5 minutes. After cooling to room temperature, an aliquot of the dispersion was analyzed. Table 2 shows the particle sizes of the samples, prepared according to Example 1, at 50 and 90 percentiles. The addition of emulsifier dramatically decreased the particle size of debranched cornstarch. However there appears to be no correlation between the amount of emulsifier and the particle size.

TABLE 2

| | Particle size (μ) | |
|---|---|---|
| Sample | 50% | 90% |
| A | 22.4 | 36.2 |
| B | 4.4 | 10.3 |
| C | 5.4 | 11.2 |
| D | 4.5 | 10.5 |

E. Viscosity

The viscosity of the hydrated starch samples were measured using a Bohlin Visco 88, Bohlin Reologi AB, Lund, Sweden. A 15% (w/w) dispersion of each starch sample (prepared according to Example 1) was prepared by mixing the starch sample in 70° C. deionized water using a kitchen blender at high speed for 5 minutes. The dispersion was refrigerated at 4° C. for 24 hours. The viscosity of the debranched cornstarch decreased with increasing emulsifier concentrations. The samples showed shear thinning behavior. No data was obtained for the sample without emulsifier (sample A) because the gel was too rigid to be measured by this instrumental technique.

TABLE 3

| Sample | Viscosity(Pas) at 17.5s$^{-1}$ |
|---|---|
| B | 3.75 |
| C | 1.37 |
| D | 0.24 |

F. Opacity

Opacity of the above dispersions after a series of dilution was measured by a spectrocolorimeter (ColorQuest 45/0, Hunter Associates Laboratory, Reston, Va). An opacity of 100% is equivalent to the opacity of the white tile used as a reference. At the same solids level, opacity increased with increasing emulsifier concentrations up to 3%. The opacity of the sample containing 6% emulsifier (D) was marginally, if at all, higher than the 3% sample (C).

Example 3
Effect of Debranching the Starch

A 15% cornstarch slurry containing 3% (by weight of starch) glyceryl monostearate was jet cooked as described in Example 1. The jet cooked material was split into two batches; one batch was enzymatically debranched using pullulanase as described in Example 1, whereas the other batch was not treated with the enzyme. After refrigeration the two samples were examined for differences in gel appearance and rheology. The debranched sample formed an opaque paste. The rheology of the paste was short and smooth, resembling that of CRISCO® brand shortening. In contrast, the sample which was not debranched gave a more elastic and less opaque gel compared to the debranched sample, resembling that of jello. The sample which was not debranched had no low molecular weight fraction and its high molecular weight fraction comprises an Mw of 7359 kd and an Mn of 294 kd. The particle size of this sample at 50% was approximately 4.5 $\mu$ and at 90% was approximately 10.5$\mu$.

Example 4
Effect of Processing Conditions

A dry blend of 75 grams of debranched cornstarch (Example 1, sample A) and 2.25 grams of glyceryl monostearate was dispersed in 425 grams of 90° C. water by mixing in a kitchen blender at high speed for 5 minutes. The dispersion was split into two batches. One batch was refrigerated at 4° C. and the other batch was autoclaved at 121° C. for 10 minutes before being refrigerated. Both samples remained liquid after 24 hours of refrigeration and gave a gritty mouthfeel when judged by a sensory panel. Thus, neither process produced a satisfactory product for use in food products.

Example 5
Addition of Emulsifier After Jet Cooking the Starch

A cornstarch slurry (15% solids) containing monoglyceride (2% by weight of starch, Myverol 18-06, Quest International, containing 90% glyceryl monostearate) was jet cooked and processed as described in Example 1 (sample 5A). Another sample (sample 5B) was prepared by jet cooking cornstarch slurry (15% solids) directly into a pre-dispersed monoglyceride dispersion (2% glyceryl monostearate, by weight of starch) followed by enzymatically debranching and drying as described in Example 1. DSC thermal analysis of the two samples gave similar melting peaks near 103° C., indicative of the presence of amylose-lipid complex. A 15% aqueous dispersion of each sample was prepared by mixing the starch-emulsifier composition in 30° C. deionized water using a kitchen blender at high speed for 3 minutes. The dispersion was refrigerated at 4° C. for 24 hours. Both samples set up as a smooth and opaque paste with similar rheological characteristics. The sensory evaluation of the two samples by trained experts is given in Table 4, where the numbers are scaled from 0 to 10, in which 0=gritty; and 10=smooth for smoothness; and 10=firm for body.

TABLE 4

| Samples | Smoothness | Body |
|---|---|---|
| 5A | 7 | 4.5 |
| 5B | 7 | 3 |

Example 6
Effect of Different Emulsifiers

Emulsifiers, such as glyceryl monostearate, sodium stearoyl-2-lactylate (SSL), sucrose monostearate, sorbitan monostearate, and polyoxyethylene sorbitan monostearate, known to complex with amylose, as well as other emulsifiers such as enzyme modified lecithin (EML), can be used in the present invention to prepare a product as described in Example 1.

SSL increases the viscosity of the jet-cooked material more than other emulsifiers and tends to form an elastic gel when cooled to 60° C. before debranching. Therefore, lower starch solids and/or higher levels of debranching enzyme are preferred when SSL is used. In general, samples made with the aforementioned emulsifiers gave typical characteristics such as small particle size, high opacity, and short, non-elastic paste structure. However differences in the extent of these properties do exist with different emulsifiers. For example, the SSL-containing sample was less opaque than samples with other emulsifiers, and sucrose monostearate gave a much smaller median particle size (1.5 $\mu$) than the typical 4–5 $\mu$ size. Table 5 summarizes some of the properties of starch-emulsifier compositions prepared using different emulsifiers.

Example 7
Co-processing with Gums

Cellulose gum such as carboxymethyl cellulose (CMC) and natural gums such as guar, alginate and xanthan gums can be co-processed with the present invention to enhance the functional properties of the composition. A sample containing 3% glyceryl monostearate was prepared as described in Example 1. An amount of CMC which A equals 10% of the starch solids was prehydrated in water at room temperature to make a 4% CMC dispersion. The dispersion was then mixed into the debranched starch-emulsifier composition in a high shear device. The mixture was then heated to 90° C. and spray dried into a fine powder. The spray drier air inlet and outlet temperatures were typically 360° F. (182° C.) and 220° F. (104° C.), respectively. The product gave similar opacity but higher viscosity compared to the sample without gum.

Example 8
Starch-Emulsifier Composition

A cornstarch slurry (10% solids) containing calcium stearoyl-2-lactylate (2.5% by weight of starch, American Ingredients Co., Kansas City, Mo.) was jet cooked as described in Example 1. The jet cooked dispersion was then spray dried under the conditions described in Example 1. A 10% aqueous dispersion of the sample was prepared by mixing the spray dried powder in 90° C. deionized water using a kitchen blender at high speed for 3 minutes. The dispersion was cooled at room temperature for 30 minutes and then refrigerated at 4° C. for 24 hours (sample 8A).

Another cornstarch slurry (10% solids) containing calcium stearoyl-2-lactylate (2.5% by weight of starch) was prepared by mixing the cornstarch into predispersed aqueous calcium stearoyl-2-lactylate. The slurry was then autoclaved at 121° C. for 30 minutes followed by cooling at room temperature for 30 minutes. The autoclaved sample was then refrigerated at 4° C. for 24 hours (sample 8B). Samples A and B were analyzed for firmness using a texture analyzer (TA XT-2, Stable MicroSystem). DSC was used to measure the thermal properties of the two samples. Results from the texture analyzer and DSC measurements are shown in Table 6.

Example 9
Effect of Different Emulsifiers on Starch-Emulsifier Complex

Emulsifiers such as glyceryl monostearate, calcium stearoyl-2-lactylate and DATEM esters known to complex with amylose, as well as others, can be used in the present invention to prepare a product as described in Example 8 (sample 8A). Three 10% refrigerated gels were prepared as described in Example 8 (sample 8A) from three starch-emulsifier compositions containing equivalent moles (2.5% based on starch weight) of calcium stearoyl-2-lactylate (sample 8A), monoglyceride (sample 9B), and DATEM esters (sample 9C). The samples were evaluated by a texture analyzer for firmness and DSC was used to measure the thermal properties of the gels. The results are given in Table 7.

Example 10
Potato Starch as Starting Material

A starch-emulsifier composition was made from potato starch and monoglyceride (2% based on starch weight) according to the method described in Example 1. A 15% aqueous dispersion of the sample was prepared as described in Example 2 using a kitchen blender. Sensory evaluation of the pastes by an expert panel showed that the paste had higher viscosity and lower smoothness scores than the cornstarch counterpart. Molecular weight distribution and thermal properties of the sample were measured by HPLC and DSC, respectively. HPLC and DSC results of the sample along with those of a cornstarch counterpart are shown in Table 8 and 9, respectively.

Example 11
Reduced-Fat Cake

A 50% reduced-fat cake was prepared with the starch-emulsifier product (3% monoglyceride) prepared according to Example 1 using the following formulation:
1. Prepare 25% starch-emulsifier paste ahead of time by mixing 25 grams dried starch-emulsifier composition with 75 grams water and refrigerating overnight.
2. Cream sugar together with shortening and starch-emulsifier paste in Kitchen Aid mixer.
3. Add sifted flour, salt and baking powder.
4. Mix for 1 minute on speed 1.
5. Scrape down sides of bowl and add eggs and milk.
6. Mix for 1 minute on speed 2.
7. Scrape down bowl and mix for 2 minutes on speed 3.
8. Bake at 350° F. (177° C.) for 25–30 minutes.

Table 10 shows the characteristics of the reduced-fat cake compared with the characteristics of the control.

Example 12
50% Reduced-Fat Cream Cheese Spread

A 50% reduced-fat cream cheese spread was prepared with the starch-emulsifier composition (3% monoglyceride) prepared according to Example 1 using the following formulation:
1. Blend 25% starch-emulsifier paste, pregelatinized starch, salt and cream cheese flavor in a Kitchen Aid mixer until smooth.
2. Add full-fat cream cheese and blend until homogenous.
3. Fill into receiving container and refrigerate.

Example 13
Fat-Free Onion Dip

A fat-free onion dip was prepared with the starch-emulsifier composition (3% monoglyceride) prepared according to Example 1 using the following formulation:
1. Blend 15% starch-emulsifier gel, starter distillate and xanthan gum with low shear until smooth.
2. Add corn protein, sour cream flavor, salt and citric acid and blend until homogenous.
3. Blend in dried onions until evenly distributed.
4. Pack and refrigerate.

Example 14
Skim Milk

A skim milk was prepared with the starch-emulsifier composition (containing 3% sucrose stearate) according to Example 6 using the following formulation:
1. Slowly add the starch-emulsifier powder to 161° F. (71° C.) milk while mixing with a kitchen blender (high speed). Continue mixing for three minutes once dispersed.
2. Add carrageenan and mix for 1 minute.
3. Homogenize through a two-stage homogenizer (2500/500 psi).
4. Cool in ice/water bath in capped bottles to 50° F. (10° C.), shake intermittently.
5. Store refrigerated.

The milk prepared as described above was compared to skim milk and whole milk. The sensory evaluation was conducted by a three-person trained expert panel, and the results are given in Table 11.

Example 15
Preparation of No-Fat Ice Cream

A no-fat ice cream was prepared with the starch-emulsifier-gum composition prepared according to Example 7 using the following formulation:
1. Funnel feed the dry ingredients, as a blend, into a recirculating stream of skim milk.
2. Preheat to 150° F. (65° C.) and homogenize through a 2 stage homogenizer; 2000 PSI (1st stage), 500 PSI (2nd stage).
3. Pasteurize at 185° F. (85° C.) for 25 seconds.
4. Age overnight at 40° F. (4° C.).
5. Add pure vanilla extract (2x) at 0.6% use rate, then freeze to 20° F. (−6° C.) with a continuous freezer (target 75% overrun).
6. Harden at −30° F. (−32° C.) for 24 hours (for quart size containers).

Example 16
Preparation of No-fat Mayonnaise

A no-fat mayonnaise was prepared with the debranched starch-emulsifier composition (containing 2% monoglyceride) prepared according to Example 1 using the following formulation:

Procedure
1. Place water (185° F.; 85° C.) in glass vessel of a kitchen blender.
2. Disperse debranched starch-emulsifier composition and corn starch as a dry blend. Slowly add the powders to the kitchen blender while mixing on maximum speed. Once dispersed, blend on high for 5 minutes to fully hydrate.
3. Add dry blend of xanthan, corn syrup solids, sugar and salt to kitchen blender, blend on high for 2 minutes, to fully disperse.
4. Transfer contents to a mini food processor, add egg yolk, color, acids and lemon juice, then process just enough to mix all ingredients.
5. Add oil, slowly, while mixing. Continue mixing for 1–2 minutes until product is smooth and homogeneous in appearance.
6. Fill containers, refrigerate overnight before evaluation.

Example 17
Preparation of Reduced-Fat Peanut Butter Spread

A reduced-fat peanut butter spread was prepared with the debranched starch-emulsifier composition (containing 2% monoglyceride) prepared according to Example 1 using the following formulation:
Procedure
1. Place ambient temperature water in glass vessel of a standard kitchen blender.
2. Slowly add starch-emulsifier composition and CMC (as a dry blend) while mixing on maximum speed. Mix for 5 minutes to fully hydrate.
3. Add sucrose, M040, salt, K sorbate (as a dry blend) and continue shear for 5 minutes.
4. Add premelted peanut butter, glycerin and color and continue mixing-at medium speed for 1 minute. Transfer to a metal container; place in a boiling water bath (185–190° F.; 85° C.–88° C.), and homogenize using a Silverson homogenizer at ¾ maximum speed for 5 minutes (small emulsor screen). Add flavor last.
5. Place in ice water bath and cool to 80° F. (27° C.) while slowly mixing with an overhead stirrer. Measure Brookfield viscosity at 80° F. (27° C.).
6. Deaerate using a WhipMix dearator.
7. Store refrigerated 2 to 3 days before evaluating.

Example 18
Fat Free Chocolate Spread

A fat free chocolate spread was prepared with the debranched starch-emulsifier composition (containing 2% monoglyceride) prepared according to Example 1 using the following formulation:
Procedure
1. Prepare blend of dry ingredients.
2. Slowly disperse blend into 195–200° F. (90–94° C.) water with a standard kitchen blender.
3. Blend on high speed for 5 minutes.
4. Add cream. Continue blending for 1 minute.
5. Deaerate using WhipMix deaerator.
6. Store refrigerated 2 to 3 days before evaluating.

Example 19
Water and Oil Absorption

The water absorption (percent by weight) was determined by a modification of American Association of Cereal Chemists Method 88-04. Instead of using 5 grams of test sample and centrifuging at 2000 g, 3 grams of sample were dispersed in water and centrifuged at 1450 g. For oil absorption, store-bought Wesson vegetable oil was used in lieu of water. Table 12 shows the water and oil absorption results for the starch-emulsifier composition (Example 1, sample C). Data for a debranched starch (Example 1, sample A) and a microcrystalline cellulose (Avicel PH105, FMC) are also presented for comparison.

Those skilled in the art will recognize or be able to ascertain, using no more than routine experimentation, many equivalents to the specific embodiments of the invention described herein. Such equivalents are intended to be encompassed in the scope of the following claims.

I claim:
1. A method for preparing a starch-emulsifier composition, comprising the steps of:
   a) heating a mixture of starch and an emulsifier in an aqueous medium under conditions sufficient to disrupt essentially all starch granules and solubilize amylose and amylopectin in the starch, to produce a dispersion of starch and emulsifier, wherein the starch has an amylose content greater than about 30%; and
   b) optionally treating the starch in the starch and emulsifier dispersion to produce a starch containing greater than about 20% short chain amylose,
thereby producing a starch-emulsifier composition.
2. The method of claim 1, wherein step (b) is performed by enzymatic treatment or acid treatment or combination thereof.
3. The method of claim 2, further comprising:
   c) heating the product of step (a) or (b) to a temperature sufficient to solubilize the emulsifier; and
   d) optionally drying the product of step (c).
4. The method of claim 1 wherein step (b) is performed using a debranching enzyme or amylase or combination thereof.
5. The method of claim 1, further comprising drying the starch-emulsifier composition.
6. The method of claim 5, further comprising adding a hydrocolloid, gum, polymer, modified starch or combination thereof.
7. The method of claim 6, wherein the hydrocolloid, gum, polymer or modified starch is selected from the group consisting of xanthan gum, alginate carrageenan, carboxymethyl cellulose, methylcellulose, guar gum, gum arabic and locust bean gum.
8. The method of claim 1, wherein the emulsifier is selected from the group consisting of monoglycerides, sorbitan esters, diacetyl tartaric acid esters of monoglycerides, enzyme modified lecithin, propylene glycol esters, polysorbates and sucrose esters of medium and long chain saturated fatty acids and combinations thereof.
9. The method of claim 1, wherein the emulsifier is selected from the group consisting of glyceryl monostearate, polyethylene glycol monolaurate, calcium stearoyl lactate, sodium stearoyl lactate, sorbitan monostearate, polyoxyethylene sorbitan monostearate, sucrose monopalmitate and sucrose monostearate.
10. The method of claim 1, wherein the amount of emulsifier is from about 0.1% to about 25% by weight.
11. The method of claim 10, wherein the amount of emulsifier is from about 1% to about 10% by weight.
12. The method of claim 1, further comprising adding a hydrocolloid, gum, polymer, modified starch or combination thereof.
13. The method of claim 12, wherein the hydrocolloid, gum, polymer or modified starch is selected from the group consisting of xanthan gum, alginate carrageenan, carboxymethyl cellulose, methylcellulose, guar gum, gum arabic and locust bean gum.
14. The method of claim 1, wherein step (a) is performed by jet cooking.

15. The method of claim 1, wherein the starch is selected from the group consisting of cornstarch, potato, tapioca, wheat, smooth pea, sago, barley and oat.

16. A method for preparing a starch-emulsifier composition, comprising the steps of:
   a) heating a starch under conditions sufficient to disrupt essentially all starch granules and solubilize amylose and amylopectin in the starch;
   b) immediately combining the product of step (a) with an emulsifier to produce a dispersion of starch and emulsifier, wherein the starch has an amylose content greater than about 30%; and
   c) optionally treating the starch in the starch and emulsifier dispersion to produce a starch containing greater than about 20% short chain amylose, thereby producing a starch-emulsifier composition.

17. The method of claim 16, wherein step (c) is performed by enzymatic treatment or acid treatment or combination thereof.

18. The method of claim 16, wherein the emulsifier is selected from the group consisting of monoglycerides, sorbitan esters, diacetyl tartaric acid esters of monoglycerides, enzyme modified lecithin, propylene glycol esters, polysorbates and sucrose esters of medium and long chain saturated fatty acids and combinations thereof.

19. The method of claim 16, wherein the starch is selected from the group consisting of cornstarch, potato, tapioca, wheat, smooth pea, sago, barley and oat.

20. The method of claim 16, wherein the emulsifier is selected from the group consisting of glyceryl monostearate, polyethylene glycol monolaurate, calcium stearoyl lactate, sodium stearoyl lactate, polyoxyethylene sorbitan monostearate, sucrose monopalmitate, sucrose monostearate and combinations thereof.

21. The method of claim 16, wherein the amount of emulsifier is from about 0.1% to about 25% by weight.

22. The method of claim 16, wherein the amount of emulsifier is from about 1% to about 10% by weight.

23. The method of claim 16, wherein step (c) is performed using a debranching enzyme or amylase or combination thereof.

24. The method of claim 16, further comprising adding a hydrocolloid, gum, polymer, modified starch or combination thereof.

25. The method of claim 24, wherein the hydrocolloid, gum, polymer or modified starch is selected from the group consisting of xanthan gum, alginate carrageenan, carboxymethyl cellulose, methylcellulose, guar gum, gum arabic and locust bean gum.

* * * * *

UNITED STATES PATENT AND TRADEMARK OFFICE
CERTIFICATE OF CORRECTION

PATENT NO. : 6,485,575 B2
DATED : November 26, 2002
INVENTOR(S) : Chienko Ronnie Yuan It is certified that error appears in the above-identified patent and that said Letters Patent is hereby corrected as shown below:

<u>Column 16,</u>
Line 7, after "sodium stearoyl lactate," add -- sorbitan monostearate, --.

Signed and Sealed this

Twenty-second Day of April, 2003

JAMES E. ROGAN
*Director of the United States Patent and Trademark Office*